US007763567B2

(12) United States Patent
Perry et al.

(10) Patent No.: US 7,763,567 B2
(45) Date of Patent: Jul. 27, 2010

(54) AGROCHEMICAL COMPOSITIONS

(75) Inventors: Richard Perry, Bracknell (GB); John Henry Nellteton-Hammond, Bracknell (GB); Guy Ramsay, Bracknell (GB)

(73) Assignee: Syngenta Crop Protection, Inc., Greensboro, NC (US)

( * ) Notice: Subject to any disclaimer, the term of this patent is extended or adjusted under 35 U.S.C. 154(b) by 286 days.

(21) Appl. No.: 10/596,281

(22) PCT Filed: Dec. 6, 2004

(86) PCT No.: PCT/GB2004/005117

§ 371 (c)(1),
(2), (4) Date: Jun. 8, 2006

(87) PCT Pub. No.: WO2005/055717

PCT Pub. Date: Jun. 23, 2005

(65) Prior Publication Data

US 2007/0135306 A1 Jun. 14, 2007

(30) Foreign Application Priority Data

Dec. 9, 2003 (GB) ................................ 0328528.5

(51) Int. Cl.
*A01N 43/40* (2006.01)

(52) U.S. Cl. ........................ 504/130; 504/133; 504/136

(58) Field of Classification Search ................. 504/358, 504/136, 139, 240, 246, 130
See application file for complete search history.

(56) References Cited

U.S. PATENT DOCUMENTS 3,755,595 A 8/1973 Goring et al.
5,562,914 A * 10/1996 Scher et al. ................. 424/408
6,734,141 B2 * 5/2004 Humble et al. .............. 504/206

FOREIGN PATENT DOCUMENTS

| | | |
|---|---|---|
| DE | 3631848 | 3/1988 |
| EP | 0664081 | 7/1995 |
| GB | 2022070 | 12/1979 |
| JP | 08053304 | 2/1996 |
| JP | 2926977 | 7/1999 |
| WO | 9701281 | 1/1997 |
| WO | 9732476 | 9/1997 |
| WO | 0221924 | 3/2002 |
| WO | 02076212 | 10/2002 |

OTHER PUBLICATIONS

A.A.El-Moursy et al.: "Some chemical additives to increase the activity spectrum of *Bacillus thuringinesis kurstaki* (Dipel 2X) against the rice moth Corcyra cephalonica" Database Accession No. 125:161097, Bulletin of the National Research Centre, vol. 21, No. 2, 1996, pp. 161-172.

K.E. Pallett et al.: "The role of light and oxygen in the actionof the photosynthetic inhibitor herbicide monuron", accession No. 92:35860, Environmental Toxicology and Chemistry, vol. 18, No. 10, 1999, pp. 2131-2137.

L.Abate et al.: "Binding of glyphosate by open-chain polyammonium cations", accession No. 131:318760, Zeitschrift Fur Naturforschung, C: Journal of Bioscience, vol. 34c, No. 11, 1979, pp. 1058-1061.

* cited by examiner

*Primary Examiner*—Johann R Richter
*Assistant Examiner*—Danielle Sullivan
(74) *Attorney, Agent, or Firm*—Thomas Hamilton

(57) ABSTRACT

The present invention relates to agrochemical compositions and in particular to aqueous agrochemical compositions containing a water soluble agrochemical active ingredient and an amine adjuvant; preferably triethylenediamine (TEDA) or a salt thereof; or tetramethylethylenedianmine (TMEDA) or a salt thereof.

17 Claims, No Drawings

AGROCHEMICAL COMPOSITIONS

The present invention relates to agrochemical compositions and in particular to an aqueous composition comprising an agrochemical active ingredient and an adjuvant.

Agrochemical active ingredients are generally utilized in combination with an adjuvant, which is frequently a surfactant. Most commonly adjuvants are added to enhance the bioperformance of the active ingredient and many such bioperformance enhancing adjuvants are known to those skilled in the art. We have now found that certain amines provide effective bioperformance enhancement of the active ingredient despite having little or no surfactant properties.

According to the present invention there is provided an agrochemical composition comprising an agrochemical active ingredient and an adjuvant, preferably triethylenediamine or a salt thereof, or tetramethylethylenediamine (TMEDA) or a salt thereof.

Triethylenediamine (TEDA) is a known compound which is commercially available to industry and with principal application in catalysis. TEDA is a strongly basic compound and may form salts with acidic or anionic species.

We have now found that, surprisingly, TEDA or a salt thereof, or TMEDA or a salt thereof, are effective adjuvants for improving the bioefficacy of agrochemical active ingredients. This is particularly unexpected since TEDA has no surfactant properties. The mechanism by which these amines act to enhance the bioperformance of an agrochemical active ingredient is not presently known. Other amines are also known compounds and, like TEDA amines of the present invention have no significant surfactant properties.

The amines of the present invention are basic compounds and if used in its basic form may be incompatible with base-sensitive agrochemicals such as paraquat and/or base sensitive formulants (such as some alcohol ethoxylates) as well as being a potential hazard to human exposure. It is preferred therefore that in normal use and in particular when used with base-sensitive agrochemicals and/or formulants, the amines of the present invention are neutralized in whole or part. The amines of the present invention may conveniently be neutralized by the addition of acid, for example a mineral acid such as a halide acid, for example hydrochloric acid or an organic acid such as acetic acid. The amines of the present invention may also however be neutralized by the addition of any suitable anionic acid species, including anionic surfactants as will be described in greater detail below.

The term "a salt of the amines of the present invention" as used herein includes the amines of the present invention whether wholly or partially neutralized by an anionic species and does not necessarily imply the physical association of the amine cation and the anionic species in the composition. It will generally be convenient to neutralize or partially neutralize the amines of the present invention prior to incorporation in the composition of the invention.

The term "agrochemical active ingredient" as used herein includes without limitation herbicides, insecticides, fungicides, plant growth regulators and seed treatment agents. It is preferred that the agrochemical compositions are aqueous compositions and it is especially preferred that the agrochemical active is a water-soluble agrochemical active. The aqueous agrochemical compositions may generally be applied to the target by spraying and the composition may be a concentrate which is designed to be diluted with water prior to application or may be ready for application. Specifically, the amines of the present invention, or a salt of the amine, may be incorporated into the spray composition prior to application as a tank mix or may form a component of an agrochemical concentrate intended for dilution prior to use. It is a particular advantage of the salts of amines of the present invention they are readily soluble in water and are generally compatible with water-soluble agrochemicals. Salts of amines of the present invention are thus particularly suitable to be "built-in" to a concentrate comprising a water-soluble active ingredient.

Suitable agrochemical active ingredients are known to those skilled in the art and are listed in standard reference books such as the Pesticide Manual. As examples of suitable water-soluble active ingredients there may be mentioned paraquat, diquat, glyphosate, fomesafen, thiamethoxam, mesotrione, and trifloxysulfuron. By the term "water-soluble" agrochemical is meant an agrochemical having a solubility in water of at least 1 g/l and preferably at least 4 g/l, for example at least 100 g/l. Of course many agrochemicals have a much higher solubility, for example 300 g/l or more or up to 500 or 600 g/l or more. Paraquat and diquat and mixtures thereof are particularly suitable water soluble agrochemical active ingredients.

Although the following description will focus on the preferred water soluble agrochemical actives, it is to be understood that other water soluble agrochemical actives may be used in the present invention.

Preferably, aqueous compositions according too the invention contain at least 40 grams per liter of paraquat or diquat or mixtures thereof (individually or in combination referred to herein as bipyridylium salt) expressed as bipyridylium ion. The compositions may contain greater than 50 grams per liter, for example greater than 100 grams per liter of bipyridylium ion. Compositions containing 200 grams or more per liter, may be prepared although a concentration of paraquat in excess of about 250 or 300 g/l tends to be unstable. In general compositions do not contain greater than 400 grams per liter of bipyridylium ion.

Thus according to a further aspect of the present invention there is disclosed an aqueous agrochemical composition comprising paraquat or diquat or a mixture thereof; and an adjuvant selected from triethylenediamine or a salt thereof, or tetramethylethylenediamine or a salt thereof. TEDA and TMEDA will hereafter be collectively referred to as the amines of the present invention.

According to a still further aspect of the present invention there is disclosed an aqueous agrochemical concentrate composition comprising paraquat or diquat and a salt of TEDA or TMEDA or a salt thereof, wherein the concentration of the paraquat or diquat is greater than 100 g/l.

Typically the pH of the paraquat or diquat composition of the invention will be from 3.0 to 8.0 and preferably from 4.0 to 8.0. In general the pH of the amine is adjusted with acid approximately to that of the paraquat or diquat composition and those nitrogen atoms of the amine which are sufficiently basic become protonated. We have found that surprisingly, while amines generally tend to represent a dermatological hazard, a much reduced problem is encountered with the partially neutralized amines used in the present invention.

While the scope of the present invention is not limited to any particular bipyridyl composition, the invention is particularly suitable for use with an aqueous formulation of a bipyridylium herbicide such as those described in WO 02/076212 A1. In WO 02/076212 there are described the use of an alginate as a pH-triggered gelling agent in the manufacture of a herbicide composition comprising a salt of paraquat, a salt of diquat or a mixture thereof. The composition further comprises an emetic and/or purgative such that a pH-triggered gel effect takes place at the acid pH of human gastric juice compositions. It is generally desirable to include one or more surfactants or adjuvants in such compositions to improve the bioperformance of the herbicide. A number of possible adjuvants are listed in WO 02/076212. Furthermore, the composition also preferably contains a purgative such as magnesium sulphate. We have now found that physical compatibility issues may arise with many of the adjuvants listed in WO 02/076212. Such compatibility issues are exacerbated at relatively high concentration of bipyridylium ion (for example greater than 100 g/l and in particular if the concentration reaches about 200 g/l or more). Furthermore, the presence of relatively high concentrations of the purgative electrolyte magnesium sulphate recommended in WO 02/076212 further increases potential compatibility difficulties. Thus WO 02/076212 recommends that when the composition of the invention contains a purgative, preferably magnesium sulphate, the concentration of magnesium sulphate is preferably from 10 to 400 grams per liter of the composition, and more preferably from 10 to 100 grams per liter. Higher concentrations of magnesium sulphate, for example up to 400 grams per liter, may be used and may continue to provide increased purgative effect but such high levels of magnesium sulphate may have an adverse effect on formulation stability. As noted above, we have found that in practice formulation stability may also be compromised at concentrations below 400 g/l, for example around 100 g/l.

It is to be understood that the term physical incompatibility in relation to adjuvants used in bipyridyl compositions indicates either gross separation of one or more components of the composition which may or may not be accompanied by a significant change in formulation rheology or bulk homogeneity. It is not necessarily essential that the composition is fully homogeneous in a strict physical sense provided that the composition is substantially homogeneous in the bulk. Thus a slight separation of a second phase may be acceptable provided that the separated phase remains fully dispersed in the bulk. If however any separated phase is not fully dispersed in the bulk, but for example rises to the surface of the composition, the composition may not show bulk homogeneity and a sample taken from one portion of the bulk may have a different composition from a sample taken from a different portion of the bulk. This is obviously undesirable for a number of reasons. The term physical compatibility indicates the reverse of physical incompatibility as defined above.

We have found for example that compositions of WO 02/076212 containing about 120 g/l paraquat ion and about 80 g/l diquat ion in the presence of an alginate and about 120 g/l magnesium sulphate heptahydrate may show physical incompatibility, when it is attempted to incorporate many of the adjuvants listed therein. Thus physical separation was observed when tallow amine ethoxylate was incorporated at levels above about 10 g/l. Two phases were formed when it was attempted to incorporate a sodium salt of dodecyl benzene sulphonate at levels above about 10 g/l. Two phases were also formed when it was attempted to incorporate sodium dioctyl sulphosuccinate even at concentrations below 10 g/l. Some physical separation was observed when it was attempted to incorporate an alkyl ethoxy carboxylate at a level of 50 g/l and it is believed that the adjuvant could be unacceptable even at lower levels than this. Very poor compatibility was observed with certain alcohol ethoxylates, even at concentrations below 10 g/l. While it may be possible to overcome or mitigate such compatibility issues by reducing the concentrations of one or more of the components or by careful blending of adjuvants, all at reduced concentrations, there is a need for an adjuvant that is compatible in the compositions described in WO 02/076212, at relatively high loadings and yet exhibits a good bioperformance enhancement which is equivalent to or not much reduced from conventional adjuvants which exhibit potential incompatibility. We have found that the amine adjuvants of the present invention, and in particular triethylenediamine (TEDA) and tetramethylethylenediamine (TMEDA), meet this need. Thus for example, TEDA is compatible with compositions of WO 02/076212 at a loading of at least as great as 60 g/l actual amine. TMEDA is compatible with compositions of WO 02/076212 at a loading of up to or about 30 g/l. While other related amines may be in the same class as TEDA and TMEDA, they are not as compatible for use in the agrochemical compositions of the present invention. For example, triethylenetetramine (TETA) is compatible with compositions of WO 02/076212 at a loading of less than 30 g/l, while ethylenediamine (EDA) is compatible with compositions of WO 02/076212 at a loading of less than 20 g/l.

According to a still further aspect of the present invention there is disclosed an aqueous agrochemical concentrate composition comprising paraquat or diquat and a salt of TEDA or a salt of TMEDA wherein the concentration of the paraquat or diquat is greater than 100 g/l and which further contains from 10 to 400 grams per liter, for example from 10 to 100 grams per liter of an electrolyte purgative such as magnesium sulphate.

According to a still further aspect of the present invention there is disclosed an aqueous agrochemical concentrate composition comprising paraquat or diquat and a salt of TEDA or a salt of TMEDA wherein the concentration of the paraquat or diquat is greater than 100 g/l and which further comprises an alginate which is a pH-triggered gelling agent, such that a pH-triggered gel effect takes place at the acid pH of human gastric juice, together with from 10 to 400 grams per liter, for example from 10 to 100 grams per liter, of an electrolyte purgative, such as magnesium sulphate.

The amines of the present invention when used as sole adjuvant may provide effective bioperformance enhancement. There may be advantages however in using the amines of the present invention in combination with a second adjuvant. The second adjuvant is preferably a surfactant. There is no particular limitation on the surfactant that may be used and numerous examples will occur to those skilled in the art. We have found that anionic, cationic, non-ionic or amphoteric surfactants may be effective.

It is of course desirable that the second adjuvant also exhibits acceptable compatibility, for example with compositions such as those described in WO 02/076212, although the second adjuvant may well be present at a lower concentration than that of the amine adjuvant of the present invention, so that this aspect may not be as crucial. As examples of suitable second adjuvants there may be mentioned alkyl polyglycosides, betaines, alkylethoxy phosphates and salts thereof, alcohol ether carboxylic acids and salts thereof, alcohol ether sulphates and salts thereof. As examples of second adjuvants that may exhibit physical incompatibility at higher concentrations but may still be acceptable if incorporated at relatively lower levels compared with the amine adjuvant, there may be mentioned alcohol ethoxylates, amine ethoxylates, amine oxides and cationics such as quaternary ammonium salts.

As examples of suitable alkylpolyglycosides (APG's) there may be mentioned for example $C_{8-10}$ alkyl polyglycosides with a degree of polymerisation of 1.5-2.0 (commercially available examples include AQNIQUE 8107-U). As examples of amine ethoxylates there may be mentioned for example $C_{12-18}$ alkyl amine ethoxylates (5-50 moles). Commercially available examples include SYNPROLAM 35X15, ETHOMEEN C25 or T25. As examples of quaternary ammonium salts and ethoxylated quaternary ammonium salts include $C_{8-18}$ alkyltrialkyl ammonium halides (commercially available examples include ARQUAD 16-50). As examples of amine oxides include $C_{12-18}$ saturated or unsaturated alkyldimethyl amine oxides (commercially available examples include AROMOX MCD-W). As examples of betaines include for example alkyldimethyl betaines and alkylamidopropyl betaines, where alkyl chain length can be $C_{12-18}$ (commercially available examples include TEGOBETAINE F50). As examples of alkylethoxyphosphates include for example $C_{4-18}$ alkylethoxy (2-10 moles) mono-, di- or sesquiphosphate esters (as acid, inorganic or organic salts). Commercially available examples include CRODAFOS T5A, N10A and GERONOL CF/AR. As examples of alcohol ether carboxylates include for example those of $C_{8-18}$ alcohol The ratio by weight of the amines of the present invention to the surfactant may ethoxylate (2-15 moles) carboxylates (as acid, inorganic or organic salts). Commercially available examples include EMPICOL CBF, CBJ, and CED-5. As examples of alcohol ether sulphates include for example $C_{8-18}$ alcohol ethoxylate (2-10 moles) sulphates (as acid, inorganic or organic salts). Commercially available examples include EMPICOL EAC70, EGC70, and ESC70.

As noted above the amines of the present invention may form a salt with an anionic surfactant or a surfactant having an acidic form. If desired, such a salt may be pre-formed by the reaction of the amines of the present invention with the anionic surfactant, for example in aqueous solution, but there is no particular need for such pre-reaction.

The ratio by weight of the amines of the present invention to the second adjuvant or co-adjuvant may vary within wide limits, for example from 50:1 to 1:50, and in particular from 10:1 to 1:10 by weight.

The ratio by weight of the amines of the present invention to the agrochemical active ingredient is preferably from 1:20 to 10:1, for example from 1:10 to 1:2. When the amines of the present invention are used in combination with one or more additional adjuvants, for example additional surfactants, the ratio by weight of the total adjuvant (amine of the present invention plus additional surfactants) is preferably from 1:10 to 10:1, for example from 1:5 to 10:1. The composition may contain further additives conventional in the art.

The invention is illustrated by the following Examples in which all parts and percentages are by weight unless otherwise stated.

EXAMPLE 1

This Example illustrates the bioperformance enhancement of paraquat in the presence of TEDA. TEDA was first neutralized with hydrochloric acid to form the TEDA hydrochloride. An aqueous formulation of paraquat dichloride containing 0.5% by weight of TEDA based on total spray volume was applied to test species *Ipomoea hederacea* (IPOHE) and *Sida spinosa* (SIDSP) at 10 and 30 g/ha (based on paraquat ion). The spray volume was equivalent to 200 L/ha The biological data (% activity) at 6 days after treatment is expressed in Table 1 as an average response over the combined rates and is compared with an equivalent formulation containing only paraquat chloride.

TABLE 1

| | % Activity | |
|---|---|---|
| | IPOHE | SIDSP |
| Composition of the Invention | 66.5 | 54.5 |
| Paraquat standard (no adjuvant) | 37.0 | 38.5 |

EXAMPLE 2

The following compositions were compared using the general procedure of Example 1. TEDA was used in the form of its hydrochloride:
1. An aqueous formulation containing paraquat dichloride and 0.5% by weight of TEDA hydrochloride based on total spray volume;
2. An aqueous formulation containing paraquat dichloride and 0.5% by weight based on total spray volume of a mixture of TEDA hydrochloride and the surfactant EMPIGEN BB and TEDA at a ratio of TEDA to EMPIGEN BB of 5:2. EMPIGEN BB is lauryl betaine supplied at a concentration of 30%. The proportions given above and below are based on lauryl betaine content.
3. An aqueous formulation (comparison) containing paraquat dichloride and 0.5% by weight based on total spray volume of EMPIGEN BB
4. An aqueous formulation containing paraquat dichloride and 0.5% by weight based on total spray volume of a mixture of TEDA hydrochloride and the surfactant AGRIMUL PG2067 and TEDA at a ratio of TEDA to AGRIMUL PG2067 of 5:2. AGRIMUL PG2067 is an alkylpolyglycoside supplied at a concentration of 70%. The proportions given above and below are based on alkylpolyglycoside content.
5. An aqueous formulation (comparison) containing paraquat chloride and 0.5% by weight based on total spray volume of AGRIMUL PG2067.

TABLE 2

| | % Activity | |
|---|---|---|
| | IPOHE | SIDSP |
| No adjuvant | 17.5 | 19.0 |
| TEDA | 64.4 | 35.8 |
| TEDA:EMPIGEN BB | 74.1 | 58.9 |
| EMPIGEN BB | 58.0 | 43.9 |
| TEDA:AGRIMUL PG2067 | 60.0 | 45.8 |
| AGRIMUL PG2067 | 13.4 | 19.9 |

It will be seen that the addition of TEDA significantly enhances the bioperformance effect obtained using the surfactants lauryl betaine and alkylpolyglycoside and also that it is effective on its own.

EXAMPLE 3

Salts of TEDA with anionic surfactants were prepared as follows: 3.1 TEDA (1 g) was mixed with EMPICOL CVH (12.5 g). No hydrochloric acid was added. EMPICOL CVH is a 90% solution of capryleth-9-carboxylic acid.
1. CRODAFOS T5A (11 g) was added to 186.5 g distilled water and TEDA (2.5 g) was added to give a clear solution. No hydrochloric acid was added. CRODAFOS T5A is ethoxy (5) isotridecanol acid phosphate ester.

The compositions were evaluated at 0.5% by weight based on total spray volume using the procedure of Example 1 and were compared with corresponding compositions containing only TEDA hydrochloride at 0.5% by weight based on total spray volume and only the surfactant at 0.5% by weight based on total spray volume.

TABLE 3

| | % Activity | |
|---|---|---|
| Composition | IPOHE | SIDSP |
| No adjuvant | 17.7 | 33.1 |
| TEDA hydrochloride | 63.8 | 45.9 |
| TEDA:EMPICOL CVH | 47.9 | 50.9 |
| EMPICOL CVH | 38.8 | 43.1 |
| TEDA:CRODAFOS T5A | 47.5 | 49.1 |
| CRODAFOS T5A | 28.8 | 28.8 |

It will be seen that the addition of a relatively small proportion of TEDA to a conventional surfactant provides a highly significant increase in activity and that the TEDA is also effective on its own.

EXAMPLE 4

The bioperformance enhancement of paraquat in the presence of amines of the present invention was evaluated. The amines tested and the results are presented in Table 4. An aqueous formulation of paraquat dichloride containing 0.5% by weight of amine (based on the weight of the parent amine and based on total spray volume) was applied using a moving track sprayer to eight representative weed species at 10, 20 and 40 g/ha (based on paraquat ion). The spray volume was equivalent to 200 l/ha.

Three replicates of each test were undertaken and the biological data (% activity where 0% represents no herbicidal effect and 100% represents complete kill) at 7 days after treatment is expressed in Table 4 as a mean over all species based on an average response over the combined rates. The results are compared with an equivalent formulation containing only paraquat chloride.

TABLE 4

| Amine of the Present Invention | Mean Activity (%) |
|---|---|
| None | 54 |
| TEDA as HCl salt | 61 |
| TETA as HCl salt | 60 |
| N,N,N',N' tetramethylenediamine as HCl salt | 59 |

EXAMPLE 5

The bioperformance enhancement of paraquat in the presence of some amines of the present invention was evaluated. Ethylenediamine (EDA), and TMEDA were two of the amines tested and the results are presented in Table 5. An aqueous formulation of paraquat dichloride containing 0.2% by weight of amine (based on the weight of the parent amine and based on total spray volume) was applied using a moving track sprayer to eight representative weed species at 10, 20 and 40 g/ha (based on paraquat ion). The spray volume was equivalent to 200 l/ha.

Three replicates of each test were undertaken and the biological data (% activity where 0% represents no herbicidal effect and 100% represents complete kill) at 7 days after treatment is expressed in Table 5 as a mean over all species based on an average response over the combined rates. The results are compared with an equivalent standard formulation containing paraquat chloride and 0.2% of an effective adjuvant blend

TABLE 5

| | Mean Activity (%) |
|---|---|
| Standard adjuvants | 57 |
| EDA as HCl salt | 54 |
| TMEDA as HCl salt | 56 |

What is claimed is:

1. An agrochemical composition comprising an agrochemical active ingredient which is paraquat or diquat or mixtures thereof and an amine adjuvant selected from triethylenediamine (TEDA) or a salt thereof and tetramethylethylenediamine (TMEDA) or a salt thereof, which amine adjuvant has no surfactant properties, and wherein the ratio by weight of the amine adjuvant to the agrochemical active ingredient is from 1:10 to 1:2.

2. The agrochemical composition of claim 1 wherein the concentration of the paraquat or diquat or mixtures thereof is greater than 100 g/l.

3. The agrochemical composition of claim 2 which further comprises from 10 to 400 grams per liter, of an electrolyte purgative.

4. The agrochemical composition of claim 3 wherein said electrolyte purgative is magnesium sulphate.

5. The agrochemical composition of claim 3 which further comprises an alginate which is a pH-triggered gelling agent such that a pH-triggered gel effect takes place at the acid pH of human gastric juice.

6. The agrochemical composition of claim 4 which comprises from 10 to 100 grams per liter of magnesium sulphate as an electrolyte purgative.

7. The agrochemical composition of claim 1 which further comprises a second adjuvant.

8. The agrochemical composition of claim 7 wherein said second adjuvant is a surfactant.

9. The agrochemical composition of claim 8 wherein said surfactant is selected from the group consisting of alkyl polyglycosides, betaines, alkylethoxy phosphates and salts thereof, alcohol ether carboxylic acids and salts thereof, alcohol ether sulphates and salts thereof.

10. The agrochemical composition of claim 7 wherein said second adjuvant is present at a lower concentration that said amine adjuvant.

11. The agrochemical composition of claim 10 wherein said second adjuvant is selected from the group consisting of alcohol ethoxylates, amine ethoxylates, amine oxides and quaternary ammonium salts.

12. The agrochemical composition of claim 11 wherein the ratio by weight of the amine adjuvant to the second adjuvant ranges from about 50:1 to 1:50.

13. The agrochemical composition of claim 12 wherein the ratio by weight of the amine adjuvant to the second adjuvant ranges from about 10:1 to 1:10.

14. The agrochemical composition of claim 11 wherein the ratio by weight of the amine adjuvant to the second adjuvant ranges from about 1:1 down to 1:25.

15. The agrochemical composition of claim 14 wherein the ratio by weight of the amine adjuvant to the second adjuvant ranges from about 1:4 to 1:15.

16. The agrochemical composition of claim 7 wherein the ratio by weight of the amine adjuvant and the second adjuvant to the agrochemical active ingredient is preferably from about 1:10 to 10:1.

17. The agrochemical composition of claim 16 wherein the ratio by weight of the amine adjuvant and the second adjuvant to the agrochemical active ingredient is preferably from about 1:5 to 10:1.

* * * * *